United States Patent
Li

(10) Patent No.: US 7,798,968 B2
(45) Date of Patent: Sep. 21, 2010

(54) AUTOMATIC DETECTION SYSTEM AND METHOD OF SPECTRAL DOPPLER BLOOD FLOW VELOCITY

(75) Inventor: Yong Li, Nanshan (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 933 days.

(21) Appl. No.: 11/317,848

(22) Filed: Dec. 23, 2005

(65) Prior Publication Data

US 2007/0043294 A1 Feb. 22, 2007

(30) Foreign Application Priority Data

Aug. 2, 2005 (CN) .................. 2005 1 0036372

(51) Int. Cl.
*A61B 8/06* (2006.01)
(52) U.S. Cl. .................. 600/455; 600/453; 600/454
(58) Field of Classification Search ............... 600/455, 600/437, 453, 454
See application file for complete search history.

(56) References Cited

U.S. PATENT DOCUMENTS

| 4,751,929 | A | | 6/1988 | Hayakawa et al. |
| 5,287,753 | A | * | 2/1994 | Routh et al. ............ 73/861.25 |
| 5,634,465 | A | | 6/1997 | Schmiesing et al. |
| 5,662,115 | A | | 9/1997 | Torp et al. |
| 5,899,864 | A | * | 5/1999 | Arenson et al. ............ 600/455 |
| 5,935,074 | A | * | 8/1999 | Mo et al. .................... 600/454 |
| 6,464,641 | B1 | * | 10/2002 | Pan et al. .................... 600/453 |
| 6,530,890 | B2 | | 3/2003 | Bang et al. |
| 2005/0004613 | A1 | * | 1/2005 | Zhang et al. ................. 607/28 |
| 2005/0080329 | A1 | * | 4/2005 | Uchibori ..................... 600/407 |

FOREIGN PATENT DOCUMENTS

JP 2000-5177 A 1/2000

OTHER PUBLICATIONS

"Non-uniform Ultrasound Speckle Phase Distribution Applied to Scatterer Spacing Estimation" Weng et al. 1990 Ultrasonics Symposium. IEEE Xplore.*

* cited by examiner

*Primary Examiner*—Ruth S Smith
*Assistant Examiner*—Christopher Cook
(74) *Attorney, Agent, or Firm*—Kory D. Christensen; Stoel Rives LLP

(57) ABSTRACT

A method and system for detecting spectral Doppler blood flow velocity are disclosed. The method comprises the steps of: obtaining Doppler signals of the flow by demodulating, filtering, and analog-to-digital converting RF ultrasonic echoes; analyzing the spectrum of the Doppler signals to obtain each of the power spectral lines of the Doppler signal varying with time; determining a threshold; and determining the frequency shift parameters or the blood flow velocity corresponding to the current power spectral line based on the threshold and the current power spectral line.

20 Claims, 3 Drawing Sheets

AUTOMATIC DETECTION SYSTEM AND METHOD OF SPECTRAL DOPPLER BLOOD FLOW VELOCITY

FIELD OF THE INVENTION

The present invention relates to ultrasound technique and, particularly to ultrasound technique of measurement of fluid velocity by the use of spectral Doppler effect and, more particularly to a method for obtaining blood flow velocity by ultrasonic diagnostic instruments and envelope detection.

BACKGROUND OF THE INVENTION

In ultrasonic imaging systems, Doppler effect has been widely used in blood flow detection. For example, in an ultrasonic system for examining heart, artery and vein by the use of ultrasonic Doppler technique, it is necessary to extract related parameters from the Doppler spectrum diagram to estimate the dynamic states of blood flow of the heart and vessels. Those parameters include peak velocity, diastolic minimal velocity, resistance index, systolic/diastolic index, and etc. The determination of many of those parameters depends on the peak velocity and mean velocity of blood flow. While the detection of the peak velocity and mean velocity of blood flow can be converted to the detection of the maximum frequency shift and the mean frequency shift of the ultrasound echo. The principle is that an ultrasonic transducer transmits ultrasonic waves into the body of the person to be examined, and receives the ultrasonic echoes returned from the body of the person; the frequency of the ultrasonic echo shifts due to the scattering of the ultrasonic waves by the moving red blood cells in the vessel, and the magnitude of the frequency shift is related to the central frequency of the transmitted ultrasonic wave and the moving velocity of the red blood cells, thus the moving states of the red blood cells can be obtained by calculation, so long as the frequency shifts of the ultrasonic echoes are measured.

FIG. 1 illustrates a basic flowchart of signal processing in a conventional ultrasound Doppler spectrum analysis system. The ultrasonic echo signal forms an RF echo signal after beam synthesis, and the RF echo signal is decomposed into two components by a demodulation module, one is an I (In-phase) component and the other one is a Q (Quadrate) component. In a pulsed Doppler signal processing system, the I and Q components are range-gated by the system, respectively, that is, the two component signals are accumulated respectively in specific time intervals; the operator selects the accumulation time interval and the length of the pulse transmitted by the pulsed Doppler system according to actual situations; while the range gating procedure is not required by a continuous wave Doppler signal processing system. The I and Q components (for the pulsed Doppler signal processing system, refer to the two range accumulated components) are further filtered by a wall filter (high pass filter), respectively, to remove the clutters caused by static or lowly moving tissues and to acquire the two component signals mainly including the echoes caused by the motion of red blood cells; and these two component signals are sent to a spectrum estimation module. The spectrum estimation module generally estimates power spectrum by the use of fast Fourier transform (FFT); and the number of points of the FFT may be 128 or 256 as well. Since the dynamic range of the estimated power spectrum is too broad, each of the estimated power spectrum should be compressed by the system to be fit into the gray scale display range, and the power spectral intensity of the corresponding time and velocity (frequency shift) is displayed on the Doppler spectrum diagram on the screen.

Since the detection of the peak velocity of blood flow is in correspondence with the detection of the maximum Doppler frequency shift, a conventional method of manual detection of peak velocity of blood flow by the use of ultrasonic Doppler spectrum diagram comprises the steps of: reserving the power spectrum diagram of several cardiac cycles first; manually tracing the peak values of the spectrum by the operator according to the power spectrum diagram on the display screen; and finally, calculating each of the parameters by a computer according to said traced peak values. The disadvantages of such manual detection are that the tracing of peak velocities by the operator is tedious and time consuming, the repeatability is poor, and the estimation accuracy is low; furthermore, the operator must stop the acquisition of Doppler signals in order to trace peak velocities during detection, thus it is unable to estimate in real time.

It is, therefore, necessary for the system in FIG. 1 to further include an automatic envelope detection module, such that the variations of the peak and mean velocities of blood flow versus time can be automatically traced and displayed on the Doppler spectrum diagram in real time. The automatic detection can be performed on the estimated power spectrum after the spectrum estimation, or it can be performed on the compressed power spectrum as shown in FIG. 1. Thus the peak velocity, mean velocity, and other related parameters of blood flow can be obtained automatically by the cardiologist in real time.

In principle, it seems relatively simple to detect the Doppler peak velocity of blood flow, and only detection of the maximum Doppler frequency shift is necessary. In fact, the detection is affected by two main factors: one factor is the inherent widening of the acoustic spectrum, because the number of data points used to estimate the power spectrum is limited (such as 128 or 256 points), the estimated bandwidth of frequency spectrum is wider than the ideal one, the power spectrums are distributed in the whole cut-off frequency band; the effect of this factor on the maximum Doppler frequency shift is difficult to be quantitatively determined. The another factor is the noise contained in the Doppler signal per se, a signal and a noise are often included in the Doppler spectrum diagram, a turning point between the signal and the noise can be found by detecting the maximum frequency shift; however, the turning point of the spectrum from noise to signal is not very obvious, the Doppler frequency shift varies rapidly during the blood ejection period of one cardiac cycle, but the variations during other periods are slow; in addition, for a specific frequency, the signal-to-noise ratio of the spectrum diagram varies with time. Therefore, various methods for automatically detecting peak velocity and mean velocity of a blood flow have been successively proposed in an attempt to overcome the above mentioned affections.

In order to accurately and steadily estimate the envelope of Doppler spectrum diagram, a boundary differentiating the Doppler spectral signal from the noise on the spectrum diagram is necessary. One of the differentiating methods is to set a threshold. Those on the spectrum diagram greater than the threshold are regarded as signals, and those lower than the threshold are regarded as noises. The threshold may be set to a certain fixed percentage of the sum of all signals and noises. Under the condition of high signal-to-noise ratio (SNR), the effect of this method is preferable. In clinical applications, this method is severely affected by SNR and bandwidth. In the case of low SNR, the noise threshold set at a fixed percentage may be lower than the actual noise level; while in the case of high SNR, the noise threshold set at a fixed percentage may be higher than the actual noise level. Because the noise estimation according to this method is realized by averaging the spectral lines adjacent to a cut-off frequency, therefore when the SNR is relatively low, the estimated peak value shifts in the positive direction; when the SNR is relatively high, the estimated peak value shifts in the negative direction. The mean threshold according to this method may vary with each of the spectral lines due to the randomness of noise, which results in variation of the estimated threshold level therewith. However, the actual mean noise level is relatively stable, thus the method for automatically tracking envelope may cause unpredicted results.

In an article "Comparison of four digital maximum frequency estimators for Doppler ultrasound", Ultrasound in Med. & Biol., Vol. 14, No. 5, pp. 355-363, (1988), Larry Y. L. et al made a comparison of four methods of estimating the maximum frequency shift of Doppler frequency, and proposed an improved percentage method (referred to as "Mixed Method"). This method comprises firstly calculating a spectral integral curve for each of the spectral lines, then analyzing the integral spectral line. Generally, the spectrum diagram energy is mainly concentrated in the lower frequency portion, thus the spectral integral curve varies quickly in the potion of lower frequencies, and slowly in the portion of higher frequencies. This mixed method comprises searching for the intersection of a predetermined straight line with the spectrum integral curve, and regards the frequency corresponding to the intersection as the maximum frequency shift; wherein, the slope of the straight line is correlated to the noise level; and the noise is estimated by a method similar to the percentage method, i.e., averaging the spectral lines adjacent to a cut-off frequency.

In an article "Comparison of the performance of three maximum Doppler frequency estimators coupled with different spectral estimation methods", Ultrasound in Med. & Biol., Vol. 20, No. 7, pp 629-638, (1994), K. Marasek et al made an improvement on the mixed method, and proposed a geometric method comprising calculating the spectrum integral curve of each of the spectral line first, then analyzing each of the integral spectral lines. This method differs from the mixed method in the method for determining the maximum frequency shift point, in which a straight line is designed, the distances from each of the points on the integral spectral line to the straight line is calculated, and the frequency corresponding to the point with the minimum distance is regarded as the maximum frequency shift.

In an article "The performance of three maximum frequency envelope detection algorithms for Doppler signals", J. vasc. Invest, 1:126-134 (1995), R. Moraes et al made an improvement on the geometric method, in which a straight line passing through the origin is designed, and the frequency corresponding to the point with maximum vertical distance between the integral curve and the straight line is regarded as the maximum frequency shift. In order to prevent inestimable errors from occurring when the signal is weak, and experimental threshold is additionally used in this method. If the signals are weaker than the threshold, the detection of maximum frequency shift is not performed, and the maximum frequency shift is directly set to the wall filtering cut-off frequency.

In the technical solution disclosed in U.S. Pat. No. 5,287, 753, Routh et al introduced an adaptive threshold envelope detection method. The basic idea thereof comprises determining the maximum frequency shift by comparing the Doppler power spectral intensity with a set threshold. In this method, the threshold can be adjusted adaptively based on the SNR of each of the cardiac cycles. This method differs from the above mentioned methods in that the method assumes the noise level and mean SNR to be relatively stable in a cardiac cycle, therefore, the mean noise level and mean SNR are determined with respect to a cardiac cycle. However, the thresholds of the previous methods acutely vary with each of the spectral lines, and thus estimated threshold levels will also vary acutely with each of the spectral lines.

The main disadvantage of the above-mentioned techniques is that: the mixed method is based on the hypothesis that the maximum frequency shift in the frequency spectrum diagram shall be less than the cut-off frequency. The mean estimated noise in the boundary portion of the spectrum diagram is significative only under this hypothesis; thus this method will be invalidated when the cut-off frequency is less than the maximum frequency shift. In addition, since the result of maximum frequency shift estimation is greatly affected by the actual estimated noise and the integral curve, when the noise threshold is set to a small value, the maximum frequency shift estimation will be relatively small, and when the noise threshold is set to a big value, the maximum frequency shift estimation will be relatively big; thus this method is greatly affected by the actual SNR and accurate estimation of noise.

In the geometric method, since the maximum frequency shift estimation is a biased estimation, the effectiveness of this method will be lowered when the cut-off frequency is less than the maximum frequency shift. This method does not estimate the noise level directly, but it is severely affected by the integral curve; when the SNR is relatively low, the integral curve fails to guarantee a relatively rapid variation when the frequency is low, and a slow variation when the frequency is high, the error of the maximum frequency estimated then will be relatively high.

In the improved geometric method, since the maximum frequency estimation is a biased estimation that is always less than the actual value, similar to the geometric method, the estimation error will be greater when the maximum frequency shift approaches the cut-off frequency. Although, in this method, a threshold is added to lower misjudgement when the signal is weak, but the selection of the threshold depends on experiments; the differential of selections is relatively great under different conditions of SNR. Similar to the geometric method, when the signal energy is relatively high and SNR is relatively low, the integral curve fails to guarantee that it varies relatively rapid when the frequency is low, and relatively slow when the frequency is high, the error of the maximum frequency estimated then will be relatively high.

In the adaptive threshold method, since the noise threshold is obtained by averaging the SNRs, and the SNRs are relatively severely affected by the signal intensity, the maximum frequency shift estimation will be affected by an incorrect estimation of the noise level. Further more, since the threshold is in relation to the result of the previous cardiac cycle envelope detection, when the Doppler spectrum diagram is relatively stable, the adjustment of the adaptive threshold can not guarantee that the threshold will converge to a stable value. A simple threshold determination method is used in the determination of the envelope, the robustness of the envelope detection will also be impaired by the relatively great undulation of the power spectrum calculated by FFT.

SUMMARY OF THE INVENTION

The object of the present invention is to provide a method and system for detecting the spectral Doppler blood flow velocity to overcome the above mentioned drawbacks of the prior art, such that the effect of the SNR and bandwidth of the signal can be reduced, and the envelope detection can be performed accurately and robustly, thereby it is advantageous for the blood flow parameters to be continuously and accurately calculated.

The present invention provides a method for detecting spectral Doppler blood flow velocity, comprising the steps of: obtaining Doppler signals of the flow by demodulating, filtering, and analog-to-digital converting RF ultrasonic echoes; analyzing the spectrum of the Doppler signals to obtain each of the power spectral lines of the Doppler signal varying with time; determining a threshold; and determining the frequency shift parameters or the blood flow velocity corresponding to the current power spectral line based on the threshold and the current power spectral line.

The present invention provides a system for detecting spectral Doppler blood flow velocity, comprising: means for obtaining Doppler signals of the flow by demodulating, filtering, and analog-to-digital converting RF ultrasonic echoes; means for analyzing the spectrum of the Doppler signals to obtain each of the power spectral lines of the Doppler signal varying with time; means for determining a threshold; and means for determining the frequency shift parameters or the blood flow velocity corresponding to the current power spectral line based on the threshold and the current power spectral line.

The basic contemplation of the present invention is that, on the basis of the adaptive threshold method, the threshold level is determined based on noise level, thereby the threshold can also stably converge when the Doppler spectrum diagram is stable, thus making the envelope detection more robust, In addition, a smoothing processing can be performed on the power spectrum calculated by FFT to reduce the envelope detection error caused by great undulation of the power spectrum.

By the use of the above-mentioned technical solutions, the threshold can be automatically converged by a simple method for updating the threshold, so as to perform the envelope detection accurately and robustly, to reduce the effect of the SNR and bandwidth of the signal, and to facilitate accurate calculation of the blood flow parameters.

DETAILED DESCRIPTION OF THE INVENTION

The present invention is further described with reference to the preferred embodiments shown in the accompanying figures.

According to an embodiment of the present invention, an automatic detection method of spectral Doppler blood flow velocity is used for measuring blood flow velocity in an ultrasonic system, comprises the steps of:

A. obtaining Doppler signals of the blood flow by demodulating, filtering and analog-to digital converting RF ultrasonic echoes;

B. analyzing the spectrum of said Doppler signals to obtain each of the power spectral lines of the Doppler signal varying with time;

C. determining a threshold; and

D. determining the frequency shift parameters or the blood flow velocity corresponding to the current power spectral line based on said threshold and the current power spectral line, until the measurement procedure is ended or all of the power spectral lines have been processed;

wherein, said threshold is correlated to the mean noise level in the previous basic time interval, which is determined by experience in the system when the system starts the measurement, and automatically updated and adjusted thereafter based on said mean noise level.

According to an embodiment of the present invention, the step of updating and adjusting the threshold is performed at time intervals of a predetermined length; said predetermined time interval comprises, but not limited to, one cardiac cycle. This is decided on the basis of hypothesis that the noise level and threshold level may remain unchanged within a basic time interval, for the following reasons that: first, the background noise mainly originates from the ultrasonic instrument system and is hardly affected by the blood flow velocity; the SNRs caused by different patients may differ greatly from one another, but when the system parameters are determined, the noise levels should be relatively consistent; second, the noise levels are different during different cardiac cycles, and will be relatively stable only when the waveform examination is relatively stable; third, the noise distribution is consistent with a certain model. It is supposed that the maximum noise energy is only in relation to the mean noise level, in order to simplify computation. Therefore, for the current spectral line in the current cardiac cycle, both the mean noise and the threshold level $T_i$ remain unvaried; but when the spectral line enters the next cardiac cycle, the mean noise and threshold level will vary.

Figure 1:
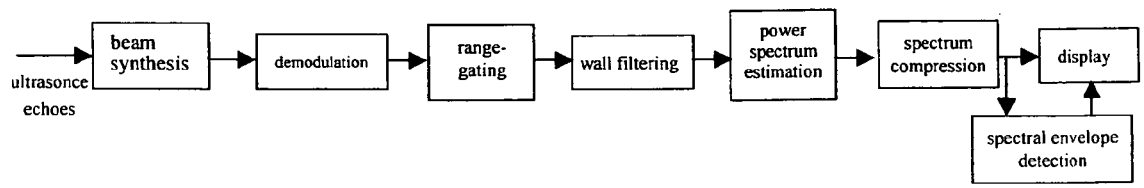
FIG. 1 shows a basic flowchart of signal processing in a conventional ultrasonic Doppler spectrum analysis system.
Figure 2:
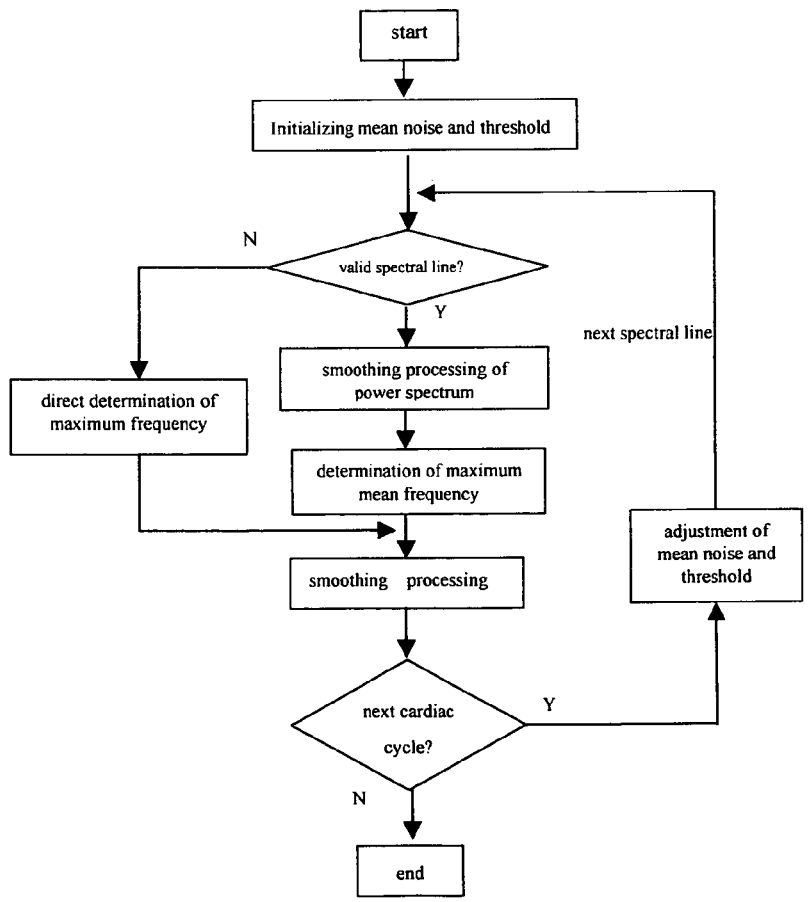
FIG. 2 shows a flowchart of the envelope detection according to an embodiment of the present invention.

The basis for calculating other parameters of blood flow by the system is the maximum frequency determined in the step D. FIG. 2 illustrates the detection procedure of the maximum frequency shift. When the system starts, the mean noise and the threshold may be initialized according to the gain level and system parameters; in the succeeding processing, each of the power spectral lines estimated by FFT is processed one by one, and with respect to each of the spectral lines, the maximum frequency shift and mean frequency shift caused by the forward and reverse blood flows, respectively, are calculated.

Figure 7:
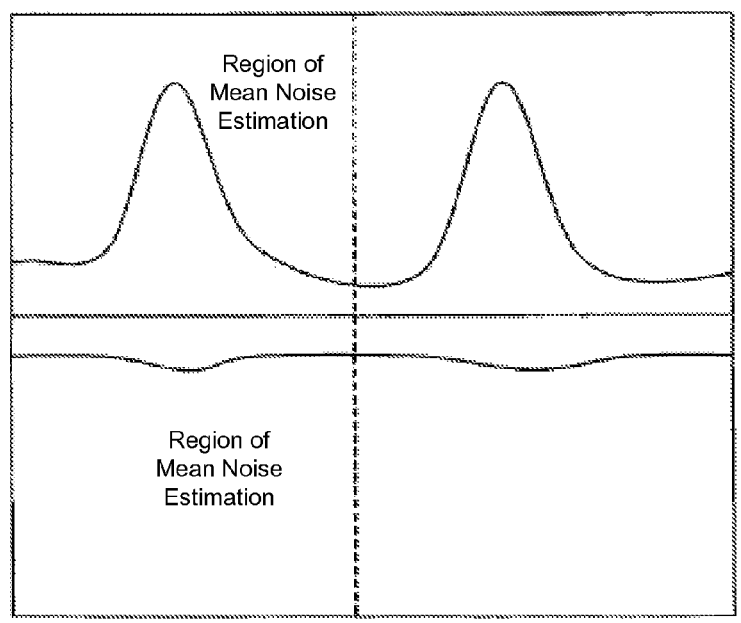
FIG. 7 shows the mean noise estimation.

The estimation of the mean noise is shown in FIG. 7 (for example, the time interval of the predetermined length is one cardiac cycle). The abscissa represent time and the ordinate represents frequency shift; the solid lines in the figure represent the calculated maximum frequency shift; wherein the solid line above the central line represents the maximum frequency shift caused by the forward blood flow; and the solid line under the central line represents the maximum frequency shift caused by the reverse blood flow. The time at the dotted line represents the end of a heart circle, at this point, the mean noise level and the threshold level are required to be recalculated, then the noise region of the calculated noise is the region outside of the maximum frequency shift. Assuming the mean noise level in the $(i-1)^{th}$ cardiac cycle is $NOISE_{i-1}$, and the threshold in the $i^{th}$ cardiac cycle be Ti, then the mean noise level $NOISE_i$ in the current cardiac cycle can be automatically updated to:

$$NOISE_i = K*NOISE_{i-1} + (1-K)* \frac{\sum_{t=t_{is}}^{t_{ie}} \sum_{f=-f_o}^{f_o} \begin{cases} l(t,f) & l(t,f) < T_i \\ 0 & l(t,f) > T_i \end{cases}}{\sum_{t=t_{is}}^{t_{ie}} \sum_{f=-f_o}^{f_o} \begin{cases} 1 & l(t,f) < T_i \\ 0 & l(t,f) > T_i \end{cases}}$$

Where l(t, f) is the spectral density, t is time, f is Doppler frequency, $t_{is}$ is the start of the $i^{th}$ cardiac cycle, $t_{ie}$ is the end of the ith cardiac cycle, $f_o$ is the cut-off frequency on the acoustic spectrum diagram, and k is a forgetting factor which can be set to 0.6-0.9 by experience. Since the threshold $T_{i+1}$ in the $(i+1)^{th}$ time interval is assumed to be related to the mean noise level $NOISE_i$ only, it can be updated automatically to $$T_{i+1} = M*NOISE_i$$

Where M is an experience constant. The calculation in this threshold updating method is simple and convergent, and an envelope can be detected stably in the situation of poor SNR.

In order to avoid the situation where an ultrasonic scanhead moves away from the body of the patient or fails to aim at the region on the body to be examined, before each time the frequency shift parameters or blood flow velocity corresponding to a power spectral line is determined in said step D, a procedure for determining whether the spectral line is valid is included; if it is determined that the spectral line is valid, the frequency shift calculation is performed, otherwise, the maximum frequency shift is determined directly.

In particular, assuming the mean noise of the previous basic time interval be $NOISE_i$, the highest peak $P(f)_{max}$ on the current spectral line is found first, then whether the current spectral line is valid is determined by comparing $P(f)_{max}$ to the mean noise level $NOISE_i$;

If $P(f)_{max}$ is less than $NOISE_i$ then the spectral line is regarded that it does not include any signal; and the detection of maximum frequency and mean frequency is unnecessary to be performed, the maximum frequency and mean frequency may be directly set to the cut-off frequency of the wall filtering.

If such situation appears in several consecutive (for example, 5) spectral lines, then the mean noise level $NOISE_i$ is reduced by half, until the $NOISE_i$ is reduced to a preset threshold; under the situation, what is received currently is regarded as a noise only, without any signal;

If $P(f)_{max}$ is within a certain predetermined range, for example, between $K_L*NOISE_i$ and $K_H*NOISE_i$ (where $K_L$ and $K_H$ are coefficients selected by experience), then it is considered that the SNR of the currently acquired Doppler signal is too small, and the detection of the maximum frequency is not very robust, the currently detected maximum frequency and mean frequency are the same as those detected previously;

If $P(f)_{max}$ is greater than $K_H*NOISE_i$, then the spectral line is determined to be a valid spectral line, and the frequency shift detection can be performed.

Where, the basic time interval represents a period of time, which may be set to (but not limited to) one cardiac cycle, in the embodiments of the present invention.

Figure 3:
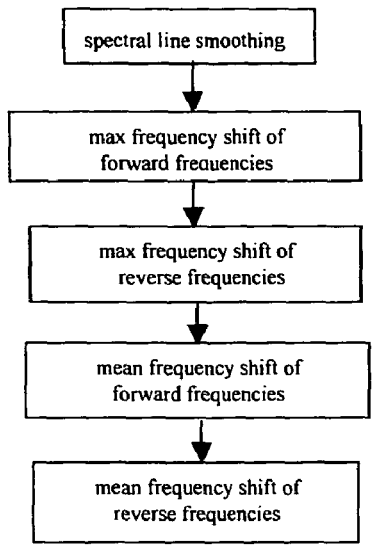
FIG. 3 shows a flowchart of detecting maximum frequency and mean frequency according to the present invention.
Figure 4:
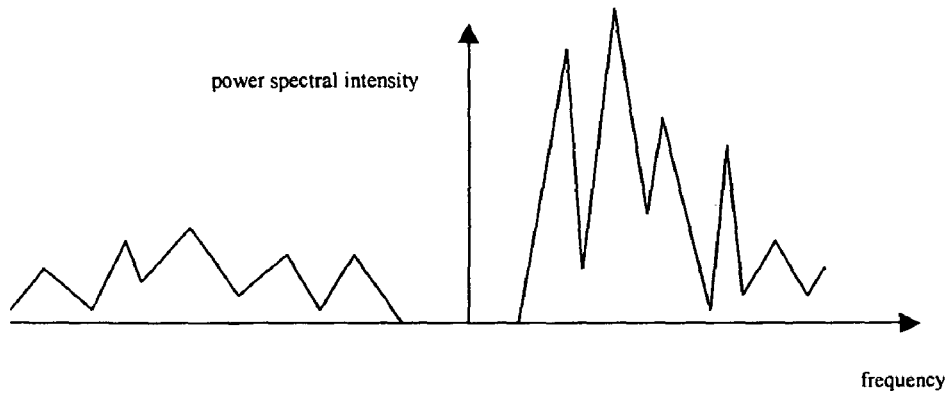
FIG. 4 shows a power spectrum before smoothing.

The flowchart of detecting the maximum frequency shift and mean frequency shift is shown in FIG. 3. Generally, the power spectrum estimated by the use of FFT may be of very large undulation, as shown in FIG. 4. The undulation can be partially reduced by the use of spectrum averaging method, but the undulation will still be relatively large, which is disadvantageous to robust performing of the succeeding envelope detection. The undulation of noise may cause the maximum frequency shift estimation on the high side, while the undulation of signal may cause the maximum frequency shift estimation on the low side.

Therefore, the embodiment of the present invention further comprises a procedure of smoothing preprocessing the power spectrum calculated by FFT prior to the detection of the maximum frequency. The smoothing processing may employ simple filtering, and can be performed prior to or after the determination of the validity of the spectral line. Assuming that the originally calculated power spectrum be $P(f_k)$, then the power spectrum $P_{average}(f_K)$ smoothing-processed can be expressed as:

$$P_{average}(f_i) = a_2 P(f_{i-2}) + a_1 P(f_{i-1}) + a_0 P(f_i) + a_1 P(f_{i+1}) + a_2 P(f_{i+2})$$

where $a_2, a_1, a_0$ are smoothing filtering coefficients.

Figure 5:
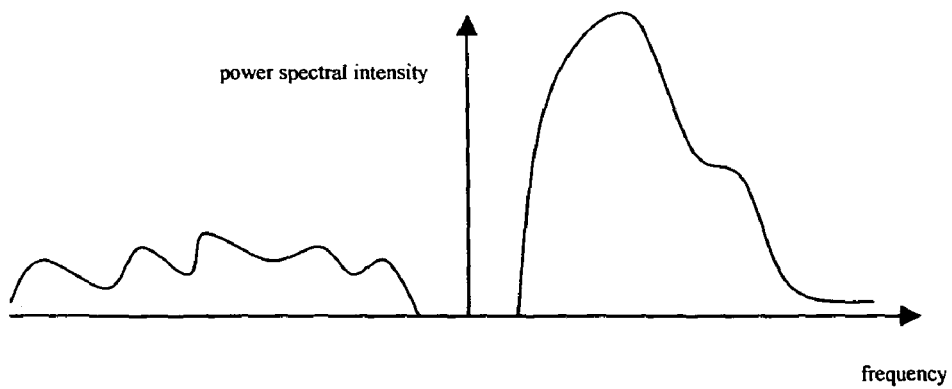
FIG. 5 shows a power spectrum after smoothing.

FIG. 5 shows the smoothed power spectrum diagram, In which, as compared with the spectrum diagram before smoothing in FIG. 4, the undulation of the power spectrum is relatively greatly removed, thus it is much smoother.

Referring to FIG. 3, when the maximum frequency is being detected, the spectral line can be divided into an upper portion and lower portion with respect to zero frequency, and the two portions are processed, respectively. The upper portion corresponds to the forward frequency shift, while the lower portion corresponds to the reverse frequency shift, so the forward and reverse frequency shifts can be detected, respectively. In the case that the forward and reverse blood flows exist at the same time, the result of such bi-directional detection is more effective.

In an embodiment of the present invention, the system determines robustly the maximum frequency based on the threshold and by using a plurality of points on the spectral line.

Figure 6:
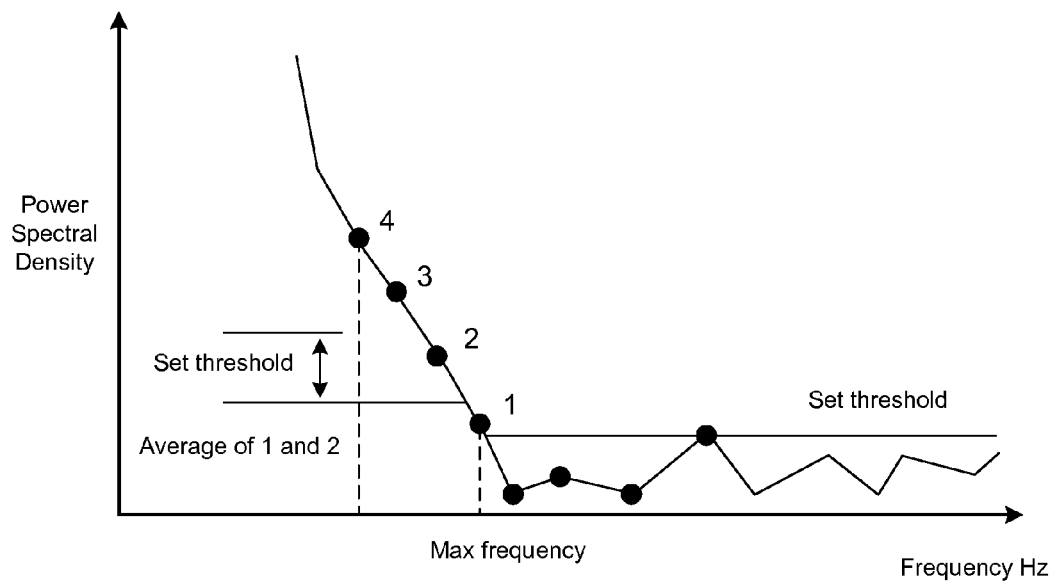
FIG. 6 shows the determination of the maximum frequency.

Assuming that the threshold corresponding to the current cardio-electric cycle is $T_i$, the determination procedure of the maximum frequency shift is illustrated in FIG. 6. The abscissa represents frequency variation, the ordinate represents power spectral density, and the curve represents the smoothed power spectrum. It is supposed that what is to be detected is the power spectrum of the forward frequency. In the higher frequency portion, the main components of the power spectrum are the estimated noise of the power spectrum and the noise of the system per se; and in the lower frequency portion, the main component of the power spectrum is the frequency shift caused by the movement of blood flow. The determination of the maximum frequency shift requires to determine the turning point from noise to signal. In particular, starting from the boundary of the acoustic spectrum diagram, a first point satisfying predetermined conditions is searched for; if it is found, the frequency corresponding to that point is the detected maximum frequency shift; and if the point is not found, then it is considered that the maximum frequency shift is less than the cut-off frequency of wall filtering.

Referring to FIG. 6, the plurality of points include, for example, four orderly consecutive points, the first point corresponding to the maximum frequency shall satisfy following two conditions: first, the power spectral densities of both the first and the second points are greater than the corresponding threshold $T_i$ in the current cardio-electro cycle; second, both the third and the fourth points are greater than a predetermined value, this predetermined value may be the sum of the mean value of the power spectral densities of the first and second points and the corresponding threshold $T_i$ in the cardio-electro cycle. The effect of the spot noises in the Doppler spectrum diagram on the envelope detection can be partially removed under these two conditions, and the result of envelope detection will be more robust. In the present embodiment, the conditions for multiple points determination according to the method of the present invention are not limited, similar multiple points determination methods under other conditions are also within the protection scope of the present invention.

After the detection of the maximum frequency shift $f_{max}$, the system may further calculate the mean frequency shift $f_{mean}$ as follows:

$$f_{mean} = \frac{\sum_{f=0}^{f_{max}} f \cdot P(f)}{\sum_{f=0}^{f_{max}} P(f)}$$

Where P(f) represent the power spectral value of frequency f.

From thus calculated the maximum frequency shift or mean frequency shift of each of spectral lines, the envelope curve of the maximum frequency shift or mean frequency shift can be further obtained.

The embodiment of the present invention as shown in FIG. 2 further comprises a smoothing processing procedure of said envelope curve, and the object of the procedure is to remove glitches on the envelope so that the detected envelope is more smooth. A median filtering method or a multiple-points smoothing method may be used. The median filtering comprises taking the median value of the envelope calculated from several consecutive spectral lines as the envelope value of the current spectral line. The multiple-points smoothing comprises performing smoothing processing on the envelope calculated from several consecutive spectral lines, and taking the result of smoothing as the final result of the envelope.

It has been prove by experiments that, in the case of various SNRs, the maximum velocity and mean velocity of blood flow can be detected robustly in real time by the use of the method and system according to present invention.

What is claimed is:

1. A method for determining frequency shift parameters relating to blood flow characteristics, comprising:
   obtaining a plurality of Doppler signals from ultrasonic echoes acquired from a patient during a first basic time interval using an ultrasonic Doppler device;
   determining a power spectral density of the Doppler signals acquired during the first basic time interval;
   analyzing the power spectral density of the Doppler signals to obtain one or more power spectral lines;
   calculating a noise threshold of the power spectral density of the Doppler signals acquired during the first basic time interval using a mean noise level of a previous basic time interval;
   calculating a mean noise level of the power spectral density of the first basic time interval using the mean noise level of the previous basic time interval, the power spectral density of the Doppler signals acquired during the first basic time interval, and the noise threshold; and
   determining frequency shift parameters relating to the blood flow characteristics corresponding to a selected one of the one or more power spectral lines using the mean noise level of the first basic time interval, the noise threshold, and the selected power spectral line, wherein the frequency shift parameters comprise a maximum frequency shift and a mean frequency shift, and wherein one or more of the frequency shift parameters determines a blood flow velocity.

2. The method according to claim 1, wherein calculating the noise threshold comprises scaling the mean noise level of the previous basic time interval by an experience constant.

3. The method according to claim 2, wherein the noise threshold is updated for each of a plurality of basic time intervals.

4. The method according to claim 3, wherein each of said basic time intervals comprises one cardiac cycle.

5. The method according to claim 2, wherein the mean noise level in the first basic time interval ($NOISE_i$) is calculated as:

$$NOISE_i = K * NOISE_{i-1} + (1-K) * \frac{\sum_{t=t_{is}}^{t_{ie}} \sum_{f=-f_o}^{f_o} \begin{cases} l(t,f) & l(t,f) < T_i \\ 0 & l(t,f) > T_i \end{cases}}{\sum_{t=t_{is}}^{t_{ie}} \sum_{f=-f_o}^{f_o} \begin{cases} 1 & l(t,f) < T_i \\ 0 & l(t,f) > T_i \end{cases}}$$

where $NOISE_{i-1}$ is the mean noise level of the previous basic time interval, l(t,f) is the power spectral density of the Doppler signals acquired during the first basic time interval; t is time; f is the Doppler frequency; $t_{is}$ is the start of the first basic time interval; $t_{ie}$ is the end of the first basic time interval; $f_o$ is a cut-off frequency; and K is a forgetting factor constant; and wherein the noise threshold is determined by scaling the mean noise level of the previous time interval by an experience constant.

6. The method according to claim 5, wherein said forgetting factor K is set to 0.6-0.9 by experience.

7. The method according to claim 1, wherein the noise threshold is determined by experience for an initial basic time interval.

8. The method according to claim 1, further comprising:
   determining whether the selected power spectral line is valid, prior to determining the frequency shift parameters;
   determining the frequency shift parameters when the selected power spectral line is determined to be valid; and
   setting the maximum frequency shift to a cut-off frequency of a wall filter when the selected power spectral line is determined to be invalid.

9. The method according to claim 8, wherein determining whether the selected power spectral line is valid comprises:
   comparing a maximum value $P(f)_{max}$ of the selected power spectral line to the mean noise level of the previous basic time interval ($NOISE_{i-1}$);
   setting the maximum frequency and the mean frequency to the cut-off frequency of the wall filter when the maximum value $P(f)_{max}$ is less than $NOISE_{i-1}$;
   reducing the $NOISE_{i-1}$ by half until it reaches a preset value when the maximum value $P(f)_{max}$ is less than $NOISE_{i-1}$ for a predetermined number of consecutive basic time intervals;
   setting the maximum frequency and the mean frequency to a maximum frequency and mean frequency of a power spectral line of the previous time interval when the maximum value $P(f)_{max}$ is between $K_L*NOISE_{i-1}$ and $K_H*NOISE_{i-1}$, where $K_L$ and $K_H$ are coefficients selected by experience; and determining that the selected power spectral line is valid when the maximum value $P(f)_{max}$ is greater than $K_H*NOISE_{i-1}$.

10. The method according to claim 1, further comprising smoothing said selected power spectral line by filtering prior to determining the frequency shift parameters corresponding to the selected power spectral line.

11. The method according to claim 1, wherein the maximum frequency shift is determined based on said noise threshold by the use of a plurality of points on the selected power spectral line.

12. The method according to claim 11, wherein said plurality of points comprise four ordinal consecutive points on the selected power spectral line, and wherein the first point corresponds to the maximum frequency when:
  power spectral density values of both the first and the second points on the selected power spectral line are greater than the noise threshold, and
  power spectral density values of both the third and the fourth points on the power spectral line are greater than a sum of a mean value of the power spectral density values of the first point and the second point and the noise threshold.

13. A system for determining frequency shift parameters relating to blood flow characteristics, comprising:
  means for obtaining a plurality of Doppler signals from ultrasonic echoes acquired from a patient during a first basic time interval using an ultrasonic Doppler device;
  means for determining a power spectral density of the Doppler signals acquired during the first basic time interval;
  means for analyzing the power spectral density of the Doppler signals to obtain one or more power spectral lines;
  means for calculating a noise threshold of the power spectral density of the Doppler signals acquired during the first basic time interval using a mean noise level of a previous basic time interval;
  means for calculating a mean noise level of the power spectral density of the first basic time interval using the mean noise level of the previous basic time interval, the power spectral density of the Doppler signals acquired during the first basic time interval, and the noise threshold; and
  means for determining frequency shift parameters relating to the blood flow characteristics corresponding to a selected one of the one or more power spectral lines using the mean noise level of the first basic time interval, the noise threshold, and the selected power spectral line, wherein the frequency shift parameters comprise a maximum frequency shift and a mean frequency shift, and wherein one or more of the frequency shift parameters determines a velocity of the blood flow.

14. The system according to claim 13, wherein calculating the noise threshold comprises scaling the mean noise level of the previous basic time interval by an experience constant.

15. The system according to claim 14, wherein the means for determining the noise threshold are configured to determine the threshold for each of a plurality of basic time intervals, and wherein each basic time interval comprises one cardiac cycle.

16. The system according to claim 14, wherein the means for calculating the mean noise level of the power spectral density comprises:

means for updating the mean noise level of the first basic time interval $(NOISE_i)$ to be:

$$NOISE_i = K*NOISE_{i-1} + (1-K)* \frac{\sum_{t=t_{is}}^{t_{ie}} \sum_{f=-f_o}^{f_o} \begin{cases} l(t,f) & l(t,f) < T_i \\ 0 & l(t,f) > T_i \end{cases}}{\sum_{t=t_{is}}^{t_{ie}} \sum_{f=-f_o}^{f_o} \begin{cases} 1 & l(t,f) < T_i \\ 0 & l(t,f) > T_i \end{cases}}$$

where $NOISE_{i-1}$ is the mean noise level of the previous basic time interval; $l(t,f)$ is the power spectral density of the Doppler signals acquired during the first basic time interval, t is time; f is the Doppler frequency, $t_{is}$ is the start of the first basic time interval, $t_{ie}$ is the end of the first basic time interval, $f_o$ is a cut-off frequency, and K is a forgetting factor constant, and wherein the means for determining the noise threshold are configured to determine the noise threshold by scaling the mean noise level of the previous time interval by an experience constant.

17. The system according to claim 13, further comprising:
  means for determining whether the selected power spectral line is valid, prior to determining the frequency shift parameters;
  means for determining the frequency shift parameters when the selected power spectral line is determined to be valid; and
  means for setting the maximum frequency shift to a cut-off frequency of a wall filter when the selected power spectral line is determined to be invalid.

18. The system according to claim 17, wherein the means for determining whether the selected power spectral line is valid comprises:
  comparing a maximum value $P(f)_{max}$ of the selected power spectral line to the mean noise level of the previous basic time interval $(NOISE_{i-1})$;
  setting the maximum frequency and the mean frequency to the cut-off frequency of the wall filter when the maximum value $P(f)_{max}$ is less than $NOISE_{i-1}$;
  reducing the $NOISE_{i-1}$ by half until it reaches a preset value when the maximum value $P(f)_{max}$ is less than $NOISE_{i-1}$ for a predetermined number of consecutive basic time intervals;
  setting the maximum frequency and the mean frequency to a maximum frequency and mean frequency of a power spectral line of the previous time interval when the maximum value $P(f)_{max}$ is between $K_L*NOISE_{i-1}$ and $K_H*NOISE_{i-1}$, where $K_L$ and $K_H$ are coefficients selected by experience; and
  determining that the selected power spectral line is valid when the maximum value $P(f)_{max}$ is greater than $K_H*NOISE_{i-1}$.

19. The system according to claim 13, further comprising means for smoothing said selected power spectral line by filtering prior to determining the frequency shift parameters.

20. The system according to claim 13, wherein the means for determining the frequency shift parameters comprise means for determining the maximum frequency shift based on said noise threshold by the use of a plurality of points on the selected power spectral line.

* * * * *